United States Patent [19]

Gueyne et al.

[11] Patent Number: 4,985,405

[45] Date of Patent: Jan. 15, 1991

[54] THERAPEUTIC PRODUCT BASED ON ORGANIC SILICON DERIVATIVES

[76] Inventors: Jean Gueyne; Marie-Christine Seguin, both of Perigord 1, 6 Lacets Saint-Leon, Monte-Carlo, Monaco; Jean-Georges Henrotte, 11 Rue de la Ferronnerie, 75001 Paris, France

[21] Appl. No.: 151,925

[22] Filed: Feb. 3, 1988

[30] Foreign Application Priority Data

Feb. 6, 1987 [FR] France ................................ 87 01446

[51] Int. Cl.$^5$ ..................... A61K 37/00; A61K 37/02; A61K 37/16
[52] U.S. Cl. ........................................ 514/008; 514/2; 514/19; 514/63; 530/360; 530/322; 548/406; 556/465
[58] Field of Search .................. 548/406; 556/465; 514/63, 8, 2, 19; 530/360, 322

[56] References Cited

U.S. PATENT DOCUMENTS

| 3,860,709 | 1/1975 | Abbott et al. | 514/63 |
| 4,328,216 | 5/1982 | Toyoshima et al. | 514/63 |
| 4,647,555 | 3/1987 | Spielvogel et al. | 514/63 |

OTHER PUBLICATIONS

C.A., vol. 75, p. 25389v, Gupyne et al., Pharmaceutical Organosilicon Complex Compositions, (1971).

Primary Examiner—Lester L. Lee
Attorney, Agent, or Firm—Ostrolenk, Faber, Gerb & Soffen

[57] ABSTRACT

Therapeutic produced based on an organic derivative of silicon, notably of silanol complexed with an amino acid, with a pharmaceutically acceptable salt of such an acid, or with a protide. The produce is suitable for the preparation of medicaments for activation and regulation of metabolism and of growth and of multiplication of cells, in particular those which are involved in the immuno-processes or in the formation of conjunctive and bone tissue.

15 Claims, No Drawings

THERAPEUTIC PRODUCT BASED ON ORGANIC SILICON DERIVATIVES

The invention concerns a new product for therapeutic use, containing as active agent one or more organosilicon compounds, more particularly silanols. The product according to the invention is particularly suitable for the preparation of medicaments which are active as activators and regulators of metabolism and of the growth and the multiplication of cells, in particular those which are involved in the immuno-processes or in the formation of conjunctive and bone tissue.

Several esters and complexes of silanols, having particular highly interesting therapeutic properties, have been described and used in the past; such is the case with, for example, monomethylsilanetriol salicylate and derivatives of glycerol and polyalkoxysilanes.

The present invention brings to the fore unforeseen applications and new therapeutic properties, mentioned above, of these products, and also new products which are more active than those which have been previously described.

The invention results from the observation that the biological activity of silicon atoms, combined in an organic form, can be modified and orientated by the nature of the molecules bonded to these atoms. Thus, the action of an organic complex cf silanol is itself all the more physiological, that is to say all the more close to the natural action of silicon in the living cell, because the silanol is bonded to a natural molecule.

The new product, according to the invention, is a complex of an organosilicon compound with a monoamino acid or with a pharmaceutically acceptable salt of such an acid. The amino acid is of the type which occurs naturally, either in the free state or combined, particularly in protides. The new product can be a definite compound.

Thus, the product according to the invention can be constituted by a complex or a definite compound, resulting from the combination of an organosilicon compound with an amino acid or with a protide. The amino acid or the protide can—of course—be substituted; this has use, in particular, in the case of acids or protides which are insoluble or scarcely soluble in water; the blockage of their acid or amine function can allow soluble compounds to be obtained.

Some amino acids suitable for the realisation of the invention are for example: serine, threonine, homoserine, tryptophan, proline, lysine, hydroxylysine, histidine, glycocoll (glycine), glutamine, asparagine, arginine, ornithine, or other non-phenolic mono-amino acids.

Among optically active amino acids, the levorotatory molecules are preferred. The products formed by the complexes of silanols with 1-serine, 1-threonine, 1-hydroxylysine, 1-lysine, for example, are particularly interesting.

The complexes according to the invention in which the amino acid is found in combined form are organosilicon complexes with protides, particularly proteins, peptides and polypeptides, of which one or more reactive group, in particular —COOH, $$\diagdown \text{CHOH} \diagup$$

and —NH$_2$ is complexed or combined with a silicon compound. Such is the case with, for example, diserine and casein. The invention covers also organosilicon complexes with protides when these are glycosylated, as is often the case with natural protides (glycoproteins, glycopeptides). Such is the case with, for example, N-acetylmuramyl-1-alanyl-d-isoglutamine, also called muramyldipeptide.

The products according to the invention can be obtained by bringing into contact, in solution or in dispersion, one or several organosilicon compounds, particularly silanols, with one or more amino acids, protides or glycoprotides, defined above.

The molar proportions of organosilicon compound and amino acid in the complex according to the invention can vary fairly widely; there can be, particularly, 0.25 to 2 atoms of Si per —COOH, $$\diagdown \text{CHOH} \diagup$$

or —NH$_2$ group of the amino acid or protein of the complex; however, the most favourable ratios are around 0.25 to 0.5 atoms of Si per —COOH, $$\diagdown \text{CHOH} \diagup$$

or —NH$_2$ group.

The organosilicon compounds and their metallic derivatives can correspond to the formula: $R_xSi(OM)_{(4-x)}$ where R is an alkyl, alkenyl or aryl, X is a number from 0 to 3, M designates an alkali metal atom or hydrogen, or an organic group having an alcohol, acid or amine function, or any other function of bonding to silicon. When R is an alkyl or an alkenyl group, it preferably contains 1 to 18 atoms of carbon or—better —1 to 4 C. If R is an aryl it is C$_6$ or C$_{10}$, without counting the C$_1$ to C$_6$ alkyl subsituents which it can carry.

Polysilanols, such as those with which publication FR 2230376 is concerned, that is to say

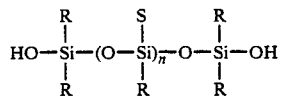

(n=0 to 20) can be used; it is however preferable to use in this case such polysilanols having a maximum of 4 Si atoms.

Organosiloxanes, useable in compounds according to the invention, are the subject of FR 1179743. In their general polymeric formula

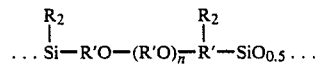

R is as defined above, R' is a $C_1$ to $C_4$ alkylene, n has a value from 0 to 20.

Monomeric siloxanes can have the structure shown in the publication FR 2484425 at pages 2 to 4, that is to say a general formula $$Z-RO-(R^1O)_n-R^2-Y$$

where at least one of the Z and Y groups is siloxanic, the other being H. Z and/or Y can thus be

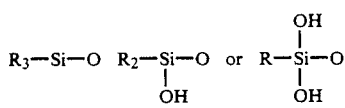

and the compound can have, for example, the form:

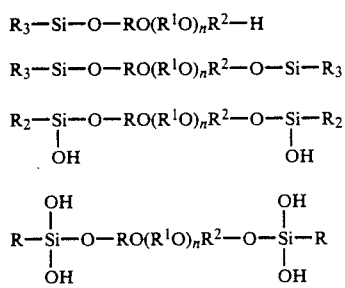

n being from 0 to 20 and most often 1 to 6.

EXAMPLE 1

Preparation of a silanol/l-threonine complex 1 liter of aqueous solution of the complex was prepared by mixing 500 ml containing 5.6 g of threonine with 500 ml of a solution of 4.4 g of methylsilanetriol; the solution contained 1.3 g Si per liter, that is to say 1 mol of $CH_3Si(OH)_3$ for 1 mol of

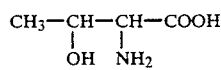

EXAMPLE 2

Preparation of a silanol/l-serine complex

To a solution of 5.3 g, that is to say 0.0504 mol, 1-serine

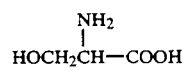

in 250 ml of water at 25° C., was added 750 ml of the aqueous solution of 4.7 g, that is to say 0.0499 mol, of methylsilanetriol $CH_3Si(OH)_3$ at 25° C. One liter of 10 g/l solution (that is to say 1% in weight/volume) of the equimolar complex

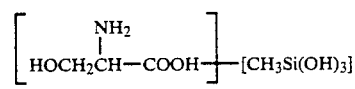

having 1 atom of silicon per —COOH or

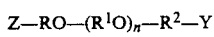

that is to say 1.4 Si per liter of solution was obtained.

EXAMPLE 3

Preparation of a silanol/diserine complex

An aqueous solution of 10 g/l was prepared starting from 6.8 g of diserine with 3.2 g of dimethylsilanediol. It contained 0.95 g Si/l.

EXAMPLE 4

Preparation of a silanol/muramyldipeptide complex

According to the process steps of the preceding examples, an aqueous solution of complex was prepared starting from 335 mg of methylsilanetriol per liter (that is to say 100 mg/l of Si) and from 360 mg of muramyldipeptide per liter. Having regard to the molecular weights of Si and of muramyldipeptide (MW≈500), this complex contained 5 atomes of silicon per molecule of muramyldipeptide.

EXAMPLE 5

Preparation of a silanolcasein complex

To a solution at pH 11 of 6.5 g of casein in one liter of water 5.4 g of ethylsilanetriol was added. The pH of the mixture was then brought back to 7 by means of HCl. Thus a solution of 1.4 g Si/liter of silanol/casein complex was obtained.

EXAMPLE 6

Preparation of a silanol/hydroxyproline complex

According to the process steps of the preceding examples, an aqueous solution of 10 g/l of complex

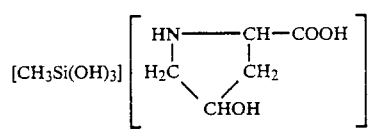

was prepared starting from 5.8 g of 1-hydroxyproline and 4.2 g of methylsilanetriol. The solution contained 1.25 g Si/liter.

EXAMPLE 7

Testing of the silanol/threonine complex with a view to its application to cell multiplication The tests were carried out on human circuitory lymphocyte cultures, coming from 25 healthy subjects, aged from 21 to 42 years. The lymphocytes were isolated according to the classical technique according to Boyum and put in suspension in the normal medium, RPMI 1640, with an added 0.5% of penicillin-streptomycin mixture and 10% of foetal calf's serum. Each of these 25 cultures was divided into four fractions A, B, C and D.

(A) Fraction A was sub-divided into three sub-fractions $A_1$, $A_2$, $A_3$ to which the solution of the complex according to example 1 was added so as to have, per liter of culture:

A1 ... 1 mg of Si

A2 ... 5 mg of Si
A3 ... 10 mg of Si

Each of these sub-fractions constituted a microculture, of which the final volume was 220 microliters, and which was incubated for 72 hours at 37° C. in an atmosphere containing 5% of $CO_2$.

(B) Three sub-fractions $B_1$, $B_2$, and $B_3$ to which was added either a solution of silanol alone (without threonine) or of silanol complex with sodium salicylate, were processed similarly. As previously, variable quantities of solution were added so as to provide per liter of culture:

B1 ... 1 mg Si/liter
B2 ... 5 mg Si/liter
B3 ... 10 mg Si/liter

The sub-fractions were then processed as in (A).

(C) To the fraction C of the initial lymphocyte culture, threonine alone (without silanol) was added in place of the complex and the sub-fractions then processed as in (A).

(D) The fourth fraction D of the initial culture had added to it neither silanol/threonine complex, nor silanol alone or silanol salicylate, nor threonine. It was incubated at 37° C. for 72 hours as in (A). Each test was carried out in triplicate.

In all the cases (A, B, C and D), 6 hours after the end of incubation, 0.5 microcuries of tritiated thymidine were added to 220 microliters of each microculture. At the end of 72 hours of incubation, the microcultures were harvested and the count of the radioactivity emitted by the tritiated thymidine was measured with a scintillation counter. The number of counts per minute of each of the microcultures made in (A), (B) and (C) was compared with the number of counts per minute obtained for the control culture (D). The ratio obtained is called the stimulation index (SI) and allows estimation of the effect on cell proliferation of the products studied, since the incorporation of thymidine in the cells is proportional to their proliferation. The effect on the proliferation is zero at $SI=1$, the effect is stimulative if $SI>1$ and if the effect is inhibitive if $SI<1$.

Under the conditions described, the stimulation index did not vary significantly with the concentration of Si (no significant differences between A1, A2, A3, etc.). The mean value of the three sub-fractions was therefore used for the following calculations. Under these conditions:

(A) The stimulation index was greater than or equal to 3 (that is to say cell multiplication was greater than or equal to 3 times that of the control cultures D) in 68% of the 25 cultures having added silanol/threonine according to example 1.

(B) The stimulation index was greater than or equal to 3 in respectively 36 and 20% of the 25 cultures carried out in the presence of silanol alone and silanol salicylate, respectively.

(C) The stimulation index was always close to 1.

It was evident from these observations that the solutions of complex according to claim 1 considerably stimulate the multiplication of lymphocytes. This stimulation is much greater than the stimulation obtained under the influence of silanol alone or of silanol salicylate. Threonine alone has no effect on the lymphocytes in culture since no modification was noted relative to the control test D ($SI \simeq = 1$).

The solution of complex according to claim 1 is usable in sealed ampoules at a concentration of 1 to 10 mg of Si per liter, intended for parenteral administration.

EXAMPLE 8

Testing of the silanol/serine complex with a view to its use to cell multiplication The solution prepared according to Example 2, was diluted with sterile water and cell cultures added so as to produce 10 m9 of Si per liter of culture. Its action was studied on cultures of human lymphoblast cells LDV/7 according to a technique similar to that of Example 7. In the short term, that is to say at the end of 24 and 48 hours, the complex diminished considerably the incorporation of tritiated thymidine into the cultures of lymphoblast cells (−68% at 24 hours and −67% at 48 hours). Silanol alone has an action which is similar but less intense (−18.5% at 48 hours). In contrast, serine on its own favours the multiplication of lymphoblast cells (+45% at 24 hours and +72% at 48 hours). The silanol serine complex and even silanol alone, thus oppose anarchic proliferation of cells of a cancerous nature, whereas serine on its own has a contrary effect In the long term, that is to say at the end of a week or two, no effect on the growth of cultures of human lymphoblast cells had been noted. On the contrary, there was formation of cellular aggregates. This suggests that the complex acts as an intercellular bonding agent or at least favourises the formation of intercellular junctions. Serine alone, silanol alone and the silanol/salicylate complex have no effect on cellular aggregation under the same operating conditions. The complex therefore normalises cultures of tumoral cells, since these are characterised by the absence of intercellular junctions, the presence of which is well-known in the cultures of healthy cells.

It was also noted that the absence of long term action of the complex on the development of lymphoblast cells can be attributed to the fact that the addition of this complex to the culture medium was done only once at time 0. The complex is therefore probably metabolised by the cells and is, after 1 or 2 weeks of culture, in a form different from the initial form. The initial aqueous solution of complex according to Example 2, containing 10 mg Si per liter, comes in the form, in particular, of 10 ml sealed ampoules It can find therapeutic applications both in man and in animal.

EXAMPLE 9

Testing of the silanol/diserine complex with a view to its use as an activating agent for the growth of cells The solution prepared according to Example 3, containing 0.95 g Si/liter, was diluted and added to cultures of human fibroblasts so as to produce 10 mg of Si/liter of culture, using a technique similar to that of Example 7. After 72 hours of culture, the added complex clearly increased the incorporation of tritiated thymidine (+122%). The effect of silanol alone was less (+72%) and that of diserine is negligeable (+15%).

The complexes according to Examples 1, 2 and 3 therefore have regulatory properties on the growth and the proliferation of cells: they stimulate the proliferation of quiescent cells (circulatory lymphocytes) but they inhibit the multiplication of cells of a cancerous nature which grow rapidly and continuously (lymphoblast cells). They also normalise the growth of the cancerous cells and promote their aggregation. Silanol alone has similar but less EXAMPLE 10

Testing of the silanol/serine and silanol/muramyldipeptide complexes with a view to their uses as activating agents for microphages and cells of the reticulo-endothelial system The experimental brucellosis infection allows testing of the activity of cells of the reticulo-endothelial system (macrophages and other cells endowed with phagocytic activity) and their capacity for destruction of intra-cellular pathogenic bacteria, such as Brucella. Female mice CD1 weighing 20 to 22 g were used. At day 1, all the animals were infected by intraperitoneal injection of 0.3 ml cf a suspension containing in total 30,000 virulent bacteria of Brucella abortus 544 After 20 days, the mice were grouped in six lots of 10 animals.

(A) The animals of lot A were then subjected to an intra-peritoneal injection of the complex prepared according to Example 2 (silanol/serine), so as to receive a total of 0.03 mg Si.

(B) and (C) Similarly, the animals of lots B and C received an identical quantity of Si administered respectively in the forms of the complex prepared according to Example 5 (silanol/muramyldipeptide) and that of silanol alone.

(D) The animals of lot D received serine alone.

(E) Those of lot E received muramyldipeptide alone and those (F) The animals of lot F, constituting the control lot, received saline. The same treatment: was repeated every day for 15 days, that is to say from the 20th to the 34th day of the experiment. At the 35th day, the animals were killed; the spleens were removed aseptically and individually ground. Seedings onto agar-agar were carried out, starting with the grindings obtained, and placed at 37° C. for 5 days. The results are expressed in the number of colonies of Brucella, obtained per hundredth of spleen The number of colonies obtained starting from the spleens of 10 animals of the control lot F is equal on average to 277. The results obtained starting from the other lots of mice are expressed in percentages of the control lot F:

|   |   | % |
|---|---|---|
| A | silanol/serine | 46 |
| B | silanol/muramyl dipeptide | 32 |
| C | silanol alone | 59 |
| D | serine alone | 96 |
| E | muramyldipeptide alone | 43 |

One sees that the silanol/serine complex (A) and to a lesser extent silanol alone (C), function as activators for macrophages (and other cells of the reticulo-endothelial system) This activation is, for silanol/serine, of the same order of magnitude as the activation obtained with muramyldipeptide alone (E) which is a well-known activator of macrophages The complex (B) of silanol with muramyl dipeptide has these effects but more strongly again.

The solutions of complexes according to Examples 2 and 4 are utilisable in sealed ampoules for therapeutic uses with a view to stimulation of the activity of macrophages of the reticulo-endothelial system and thus to stimulate the immuno-defences of the organism

EXAMPLE 11

Testing of silanol casein complex with a view to its use as a regeneration agent for dermal and sub-dermal conjunctive tissue The solution, prepared according to Example 5 of silanol/casein complex was applied cutaneously. This solution constitutes, in particular, a product which is efficacious against wrinkles which it suppresses or attenuates in stimulating growth of conjunctive tissue and the production of elastic fibres and collagens. This phenomenum must be close to the action of silanol/diserine on the growth and multiplication of fibroblasts in culture (Example 9) and that of silanol/serine on the activation of macrophages (Example 10), since it is known that activated macrophages themselves produce various local hormones which stimulate the increase of fibroblasts and the production of elastic fibres and collagens.

EXAMPLE 12

Testing of the silanol/hydroxyproline complex with a view to its use as a therapeutic agent of osteoporosis The solution prepared according to Example 6 of silanol/hydroxyproline complex was injected intraperitoneally into 15 female rats aged from 2 years, at a concentration of 0.2 ml, that is to say 0.25 mg of Si per animal every 2nd day for 3 months (lot A). Silanol alone (lot B), hydroxyproline alone (lot C) and saline (lot D) were administered in the same manner to three other lots of 15 female rats of the same age. After three months of treatment, the animals were killed, an hitological examination was carried out on the iliac fossa to measure the osseous trabecular (in % of the total surface) and the total calcium was determined on the femur of each animal.

RESULTS

| Lot of rats | Product | Variations (%) trab. Volume | |
|---|---|---|---|
| Calcium | | | |
| A | Silanol/hydroxyproline | +24 | +15 |
| B | Silanol alone | +18 | +12 |
| C | Hydroxyproline alone | +3 | −2 |

(variations expressed in % of values of the control lot (D)

Silicon is known to play an important role in the phenomenon of bone calcification; more over, hydroxyproline is an amino acid necessary for the formation of the organic matrix of the bone The results obtained show that silicon administered in the form of silanol augments the processes of bone calcification of senescent rats, subjected to calcification of senescent rats, subjected to osteoporosis. The silanol/hydroxyprotein complex according to Example 7, has effects which are more pronounced than with silanol alone, suggesting the role of hydroxy proline as possible vector of silicon in the osteoblast, cells responsible for the calcification of bones. The solution at 1.25% obtained according to Example 7 constitutes a medicament for treatment of osteoporosis.

In conclusion, Examples 7 to 12 bring to the fore new properties of silanol complexed with protides; the majority of these new properties are equally manifested but to a lesser degree by silanol alone. These new biological activities concern regulation of the growth and multiplication of human cells in culture (stimulation of quiescent cells, inhibition of tumoral cells), normalisation of the development of tumoral cells, notably aggregation of cells in culture, and activation of macrophages (and other reticulo-endothelial cells) and osteoblasts. These various effects bring about secondarily a generalised immuno-stimulation, consequential to the multiplication of lymphocytes and the activation of macrophages; they produce a regeneration of conjunctive tissue, consequential to the multiplication of fibroblasts and the production of elastic fibres and collogens, directly and/or indirectly by the activation of macrophages; they also have a favourable action on bone calcification. The solutions of Examples 1 to 7 and of other similar ones, as defined according to the invention, thus constitute immuno-stimulative, anti-tumoral, regenerative and recalcificant medicaments. Among the other therapeutic applications possible for these products, the utilisation by way of adjuvant of these vaccines, to stimulate the production of antibodies introduced thereby, can be mentioned. The effects produced by immuno-stimulation are effective as much against bacteria as against viruses.

EXAMPLE 13

Tests of the silanol serine complex on the proliferation of bacteria

The solution of 10 g complex per liter prepared according to Example 2, containing 1 gSi/l, was diluted and added to a culture of Mycrobacterium aurum so as to produce 10 mg Si per liter of culture. Neither silanol/serine, nor silanol alone, nor serine alone modified the growth of Mycobacterium aurum.

One thus sees that the aminoacid/silanol complexes, and also silanol alone, do not have the same effects on the multiplication of bacteria as those of Examples of 7 to 9 on human cells.

We claim:

1. A therapeutic product, comprising an aqueous solution containing an organic silicon derivative selected from the group consisting of silanol, polysilanol and organosiloxane and (b) a compound selected from the group consisting of protide and non-phenolic amino acid and pharmaceutically acceptable salts thereof, the ratio of (a) to (b) being 0.25 to 2 atoms of silicon per free or combined carboxylic acid group in said compound.

2. Product according to claim 1, characterised in that the organic silicon derivative is a silanol of the formula $$R_xSi(OM)_{(4-x)}$$

where R is an alkyl, alkenyl or aryl, x a number from 1 to 3, M designates an alkali metal atom or hydrogen.

3. Product according to claim 2, characterised in that the amino acid is selected from those which occur naturally in free or combined form.

4. Product according to claim 2, characterised in that the amino acid which it contains is levorotatory.

5. Product according to claim 2, characterised in that it contains 0.25 to 0.5 atoms of Si of the organic silicon derivative per —COOH group.

6. Product according to claim 2, characterised in that the amino acid is serine, theronine, homoserine, diserine, hydroxyproline or hydroxylysine.

7. Product according to claim 5, characterised in that the amino acid is lysine, histidine, glycine, glutamine, tryptophan, asparagine, arginine or ornithine.

8. Product according to claim 2 characterised in that the protide is glycosylated.

9. The product according to claim 2, characterized in that the protide is casein.

10. The product according to claim 8, characterized in that the glycosylated protide is muramyl dipeptide.

11. The product according to claim 2, wherein R is a 1 to 4 carbon atom alkyl group.

12. The product according to claim 11, characterized in that the organic silicon compound is methylsilanetriol or ethylsilanetriol.

13. The product according to claim 2, characterized in that the silanol is methylsilanetriol and said compound is L-threonine, L-serine, muramyl dipeptide or hydroxyproline.

14. The product according to claim 2, characterized in that the silanol is dimethylsilanediol and said compound is diserine.

15. The product according to claim 2, characterized in that the silanol is ethylsilanetriol and said compound is casein.

* * * * *